United States Patent [19]
Cleator

[11] Patent Number: 5,948,687
[45] Date of Patent: *Sep. 7, 1999

[54] DEVICE AND METHOD FOR SCREENING FECAL OCCULT BLOOD SPECIMENS

[76] Inventor: Iain G.M. Cleator, 1051 Laurier Ave., Vancouver, B.C., Canada, V6H 1Y2

[*] Notice: This patent is subject to a terminal disclaimer.

[21] Appl. No.: 09/022,007

[22] Filed: Feb. 11, 1998

Related U.S. Application Data

[63] Continuation-in-part of application No. 08/658,543, Jun. 5, 1996, Pat. No. 5,747,344.

[51] Int. Cl.$^6$ .................................................. G01N 33/72
[52] U.S. Cl. ............................ 436/66; 422/55; 422/56; 422/57; 422/58; 422/61
[58] Field of Search .................... 422/55, 56, 57, 422/58, 61; 436/66

[56] References Cited

U.S. PATENT DOCUMENTS

| | | | |
|---|---|---|---|
| 3,996,006 | 12/1976 | Pagano | 422/58 |
| 4,225,557 | 9/1980 | Hertl et al. | 422/56 |
| 4,259,954 | 4/1981 | Levine | 128/638 |
| 4,365,970 | 12/1982 | Lawrence et al. | 436/66 |
| 4,367,750 | 1/1983 | Levine | 128/638 |
| 4,645,743 | 2/1987 | Baker et al. | 436/66 |
| 4,742,002 | 5/1988 | Guadagno | 435/28 |
| 4,747,344 | 5/1988 | Cleator | 436/66 |
| 4,782,629 | 11/1988 | Baker et al. | 435/7 |
| 4,808,379 | 2/1989 | Wardlaw et al. | 422/56 |
| 5,100,619 | 3/1992 | Baker et al. | 422/58 |
| 5,106,582 | 4/1992 | Baker | 422/58 |
| 5,171,529 | 12/1992 | Schreiber | 422/58 |
| 5,182,191 | 1/1993 | Fan et al. | 435/7.9 |
| 5,196,167 | 3/1993 | Guadagno et al. | 422/56 |
| 5,238,847 | 8/1993 | Steinbiss et al. | 436/64 |
| 5,310,680 | 5/1994 | Baker et al. | 436/66 |
| 5,391,498 | 2/1995 | Baker et al. | 436/66 |

*Primary Examiner*—Jill Warden
*Assistant Examiner*—S. Carrillo
*Attorney, Agent, or Firm*—Nixon & Vanderhye

[57] ABSTRACT

A specimen testing device having first and second panels and a reagent sheet therebetween. The first panel has an aperture with a cover and the second cover has an aperture opposite the aperture in the first panel. The sheet in the first aperture has first and second portions disposed on opposite sides of a longitudinal axis of the panel and a fecal specimen is smeared on the sheet in the apertures so as to cover the first and second portions. The second panel is provided with a cover which overlies the first portion of the sheet and with a further cover which overlies the second portion of the sheet. The further cover is selectively moveable depending on the outcome of testing of the sample on the first portion through the respective aperture on the second panel.

17 Claims, 7 Drawing Sheets

Fig. 5

DEVICE AND METHOD FOR SCREENING FECAL OCCULT BLOOD SPECIMENS

CROSS-REFERENCE TO RELATED APPLICATION

The present application is a continuation-in-part application of application Ser. No. 08/658,543, filed Jun. 5, 1996 (herein incorporated by reference), now U.S. Pat. No. 5,747,344.

The present invention relates to a device for determining the presence of occult blood in fecal matter, and to a method of testing using such a device.

BACKGROUND OF THE INVENTION

For many years it has been recognized that colorectal cancer and large polyps bleed into the stool. Use of guaiacum for the detection of blood was described in "The Scarlet Letter" by Sherlock Holmes as being sensitive but unreliable. The problem has been that guaiacum detects oxidizing agents of which blood is only one, and red meat and other oxidizing agents also can test positive.

A typical form of fecal occult blood testing known as Hemoccult II® utilizes a guaiac-treated test sheet upon which a specimen of fecal material is smeared. A developing solution is applied to the opposite side of the sheet yielding a blue color which suggests that blood may be present in the fecal specimen. The drawback of this approach is that a high percentage of false positives is obtained from patients who in fact do not have a cancer or polyp. A false positive result in the test often results in expensive testing of patients who in fact have simply consumed a lot of meat just prior to the test.

One approach to overcome the high incidence of false positives has been to make the test paper sensitive enough to detect up to 2% of blood but not sensitive enough to produce too many false positives. A disadvantage of this compromise approach is that because of the reduced sensitivity, a number of cancers and polyps are not detected.

In an effort to increase sensitivity, the Hemoccult® SENSA system was devised. However, this system results in a higher incidence of false positives requiring unnecessary invasive tests.

Alternative approaches to cutting down on false positives have involved placing patients on specific diets designed to restrict intake of animal proteins and other sources of false positives. Despite these efforts, large numbers of false positives still occur. One reason for this is the very long time it can take for food to pass through the bowel in certain patients.

A specific test for human hemoglobin has been devised. This test—the HemeSelect® test—theoretically registers only human hemoglobin and not animal blood from meat or other agents and therefore theoretically does not require the patient to be on a special diet. Another possible advantage is that human blood from the upper gastrointestinal tract may be digested by the time it reaches the stool and the only human blood detected would be that from the distal bowel. A serious drawback of the HemeSelect® test is that it is expensive for a screening test and requires specially trained individuals to perform and read the test.

A need therefore exists for an inexpensive and easy-to-use test which has a minimal incidence of false positives and can be readily used in a doctor's office. The invention of the present application meets that need.

SUMMARY OF THE INVENTION

In accordance with one aspect of the present invention, there is provided a testing device including a first panel, a first aperture in the first panel, a second panel and a second aperture in the second panel opposite the first aperture. A sheet is deposed between the first and second panels for receiving a specimen through the first aperture. The sheet has first and second portions disposed on opposite sides of a longitudinal axis of the first panel onto which the specimen is placed. A first aperture cover is mounted on the first panel and overlies the first aperture. A second aperture cover is mounted on the second panel and overlies the first portion of the sheet. A third aperture cover is also mounted on the second panel and overlies the second portion of the sheet. The second and third covers are movable independently of each other to selectively expose the first and second portions of the sheet.

According to a preferred aspect, the first and second apertures are rectangular and extend transversely across the first and second panels. The first cover is preferably hingedly mounted along a hinge line extending transversely of the first panel, and the second cover is preferably hingedly mounted along a hinge line extending longitudinally of the second panel. The third cover is preferably hingedly mounted along a hinge line extending longitudinally of the second panel.

The sheet may be a single piece of paper, typically filter paper, with a hydrophobic dividing strip separating the first and second portions to prevent or minimize possible leakage of developing solution from the first portion to the second portion. Alternatively, the first and second portions may be comprised of two separate pieces of filter paper separated by a hydrophobic barrier. The paper sheet may be impregnated with reagent (e.g. guaiac) over the entire area thereof, or may be impregated with reagent (guaic) only on the first portion and plain unimpregnated filter paper for the second portion. The hydrophobic material may be wax or other suitable solid organic material.

In another preferred aspect, the first and second portions are provided with indicating means for locating where specimen is to be placed on the sheet through the first aperture and where developing solution is to be placed on the first portion through the second aperture. The indicating means may comprise printed circles or other shapes on the sheet as a visible indicator to the user of where to place the specimen. At least one of the indicating means, usually that in the second portion, is preferably comprised of a perforated zone which is removable from the sheet. Preferably, the third cover overlies the removable zone.

In accordance with a particularly preferred aspect of the invention, the first panel has three apertures extending transversely of the first panel and the second panel has two apertures opposite the three apertures which extend longitudinally of the second panel. A support panel for the sheet is provided between the first and second panels with apertures corresponding to the apertures in the first panel. Each of the three apertures in the first panel has a respective cover hingedly mounted along a hinge line extending transversely of the longitudinal axis of the panel and overlying a respective aperture and respective first and second portions of the sheet. A single second cover is hingedly mounted on the second panel along a hinge line extending longitudinally of the second panel and overlies the three first portions. A single third cover is hingedly mounted on the second panel along a hinge line extending longitudinally of the second panel and overlies the three second portions. The second and third covers are selectively movable with respect to each other to expose the first and second portions as desired.

According to another preferred feature, the device may carry printed matter on the first panel such as patient details and instructions for opening of the respective covers to reveal the apertures on which the specimen is smeared. Printed matter may also be provided on the second panel, such as instructions to the doctor for conducting testing of specimens.

A further preferred feature of the device is that sticking of the cover to the specimen is prevented by providing the inside surfaces of the respective aperture covers with a non-stick coating, such a wax layer.

According to yet another aspect of the invention, there is provided a method of analyzing a specimen using a specimen testing device according to the invention. The method includes the steps of obtaining a specimen, for example a fecal specimen, opening an aperture cover on the first panel, smearing a portion of the specimen on the first and second portions of the sheet through the first aperture, and closing the first aperture cover to overlie the aperture and the specimen on the sheet. A first analysis of the specimen is carried out by opening the aperture cover on the second panel to expose the first portion of the sheet carrying the specimen and applying a reagent to the exposed first portion through the second panel. Depending on the outcome of the first analysis, the other aperture cover on the second panel is selectively opened to expose the second portion of the sheet carrying the specimen and further analysis is carried out, for example in a laboratory.

In another embodiment, the invention provides a panel suitable for use in a specimen testing device. The panel includes a plurality of first apertures on a first portion disposed on one side of a longitudinal axis, with each of the apertures having a cover. A plurality of second apertures are provided on a second portion disposed on the other side of the longitudinal axis, with each of the second apertures having a cover, and with the first apertures being disposed opposite to the second apertures. Each of said first apertures on said first portion has an axis extending transversely of said longitudinal axis, and each of the second apertures on said second portion has an axis extending longitudinally of the longitudinal axis. A fold line extends parallel to the longitudinal axis, and is positioned such that when the panel is folded along the fold line, the first portion overlies said second portion and the apertures in said first portion are opposite the apertures in said second portion.

The invention further provides a specimen testing device comprising a panel as defined above folded along the fold line with the first and second portions overlying each other, and a specimen receiving sheet sandwiched between the overlying first and second portions. The specimen receiving sheet typically has at least one hydrophobic strip defining specimen receiving regions which are accessible through the apertures. More usually, the sheet has a hydrophobic strip extending longitudinally of the sheet and at least one hydrophobic strip, more usually two strips, extending transversely on and crossing the longitudinally extending strip.

The present invention enjoys numerous advantages. In particular, the device is embodied in one card which readily facilitates transference between the doctor and the patient and between the doctor and another testing location, such as a laboratory. The device is easy to use by the patient and is inexpensive to produce. A particularly important advantage is that the device allows a first test to be carried out by the doctor and, in the event that a specimen is positive, subsequent testing can be carried out on the same specimen.

BRIEF DESCRIPTION OF THE DRAWINGS

The invention will now be described with reference to the accompanying drawings, in which:

Figure 5:
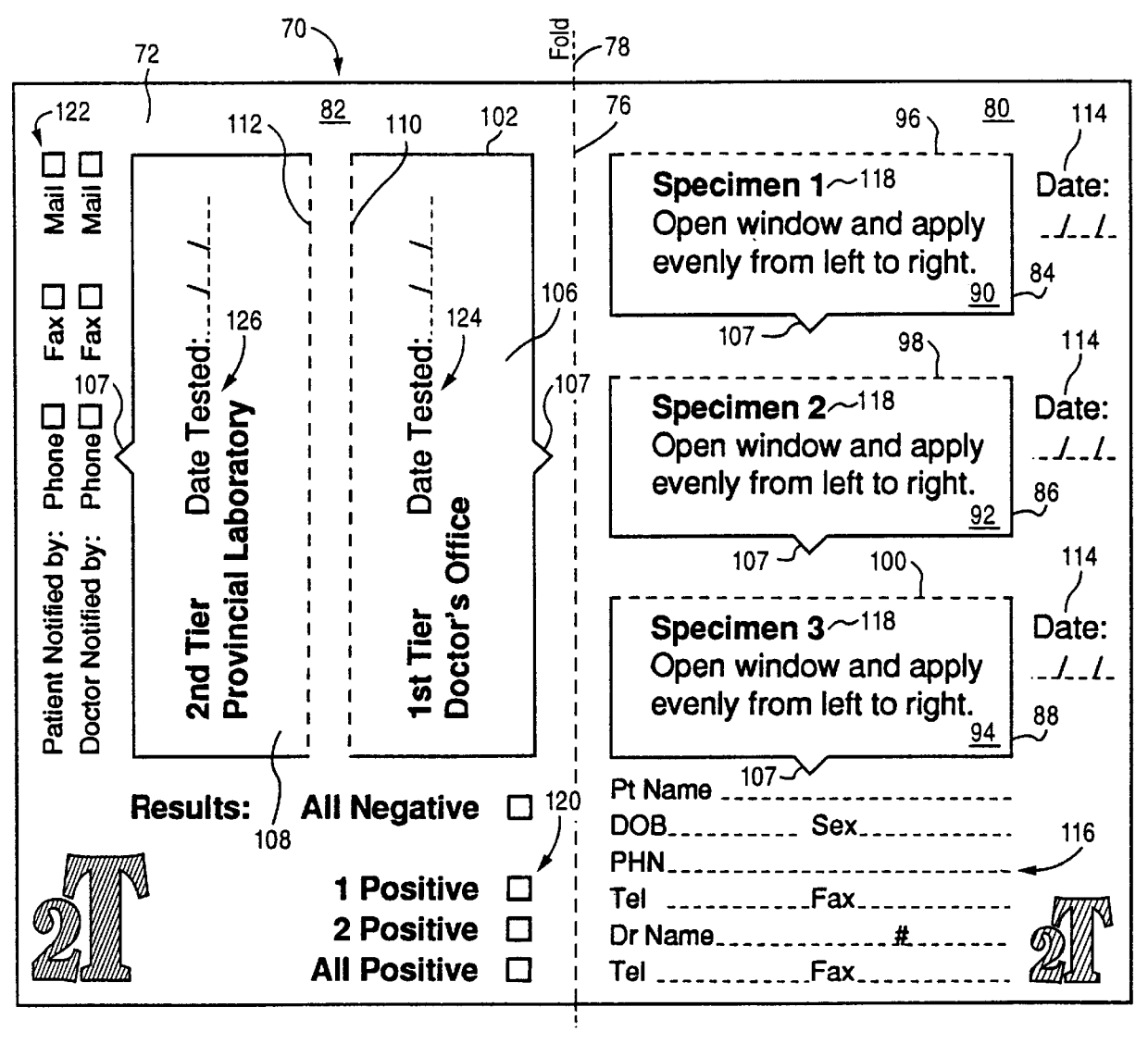

FIG. 5 is a plan view of a filter embodiment showing the outside configuration of a foldable panel.

DETAILED DESCRIPTION OF PREFERRED EMBODIMENTS

Figure 1:
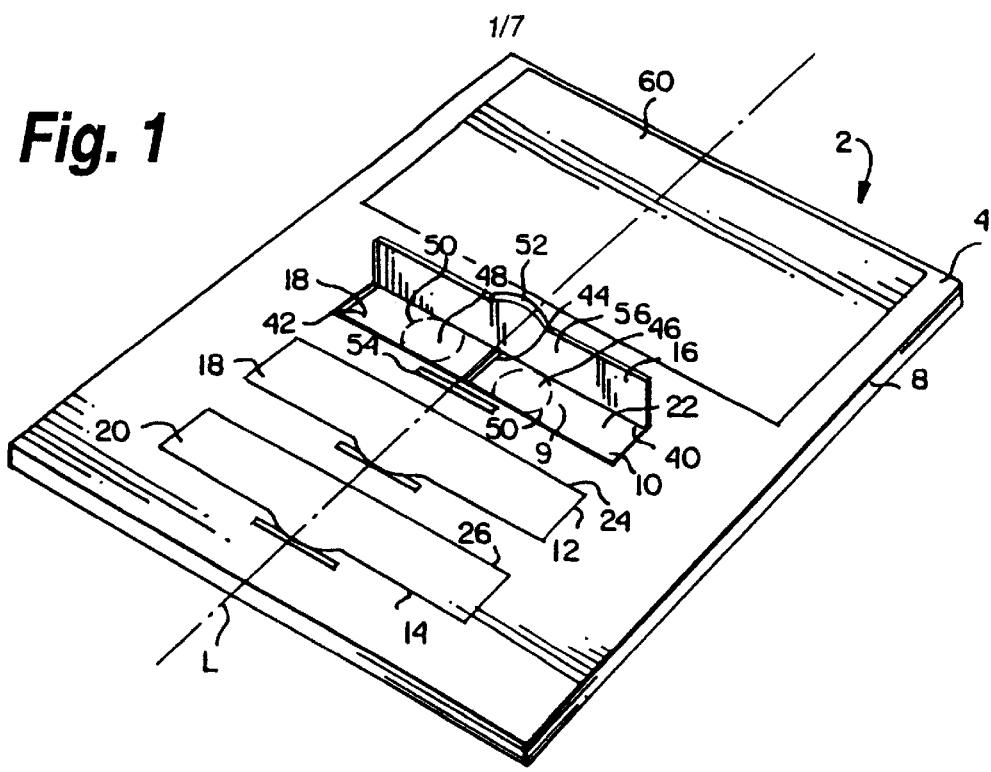
FIG. 1 is a perspective view of the device of the invention showing one cover in the open position.
Figure 2:
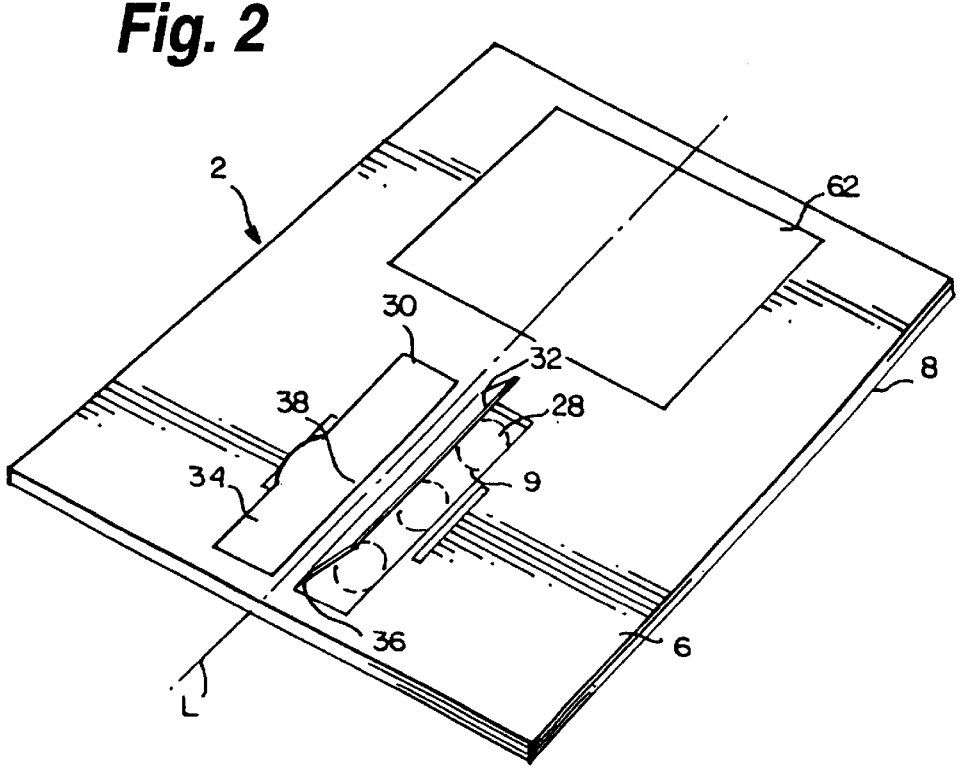
FIG. 2 is a perspective view of the device of FIG. 1 as viewed from the other side and showing one cover in the open position.

Referring to FIGS. 1–3, where like numbers refer to the same elements, a device of the invention, generally referenced 2, is shown which includes first and second panels 4, 6 with a support panel 8 disposed between the first and second panels 4, 6 carrying a absorbent sheet 9 on which a specimen is placed. The first panel 4 has three rectangular apertures 10, 12, 14 extending transversely of a longitudinal axis L of the first panel. Each aperture has a respective cover 16, 18 and 20 hingedly mounted to the first panel along a hinge line 22, 24, 26 extending transversely of the longitudinal axis L. Each cover 16, 18, 20 is hingedly movable independently of the other between a closed position as shown for covers 18 and 20 where the cover overlies the aperture, and an open position as shown for cover 16 where the aperture 10 and underlying sheet 9 are exposed.

The second panel 6 includes two rectangular apertures 28, 30 extending longitudinally of the longitudinal axis L and positioned opposite the transversely extending apertures 10, 12, 14 in the first panel 4. Aperture 28 is provided with a cover 32 and aperture 30 is provided with a cover 34. Covers 32 and 34 are each hingedly mounted along a respective hinge line 36, 38, each of which extends parallel to longitudinally axis L of second panel. Each cover 32, 34 is movable independently of each other between a closed position as shown for cover 34 where the cover overlies the aperture 30, and an open position as shown for cover 32 where the aperture 28 and underlying sheet 9 are exposed.

The support panel 8 is positioned between the first and second panels 4, 6 and supports sheet 9. Sheet 9 is made of an absorbent material, and is typically filter paper impregnated with a reagent which will react with hemoglobin components from blood and a peroxide solution to form a colored compound. Examples of suitable reagents are guaiac, tetramethyl benzidene, orthotoluidine and other similar chromogens. In the embodiment illustrated herein, the reagent impregnated in sheet is guaiac. The support panel 8 has apertures 11 corresponding to the apertures in the first panel.

Figure 3A:
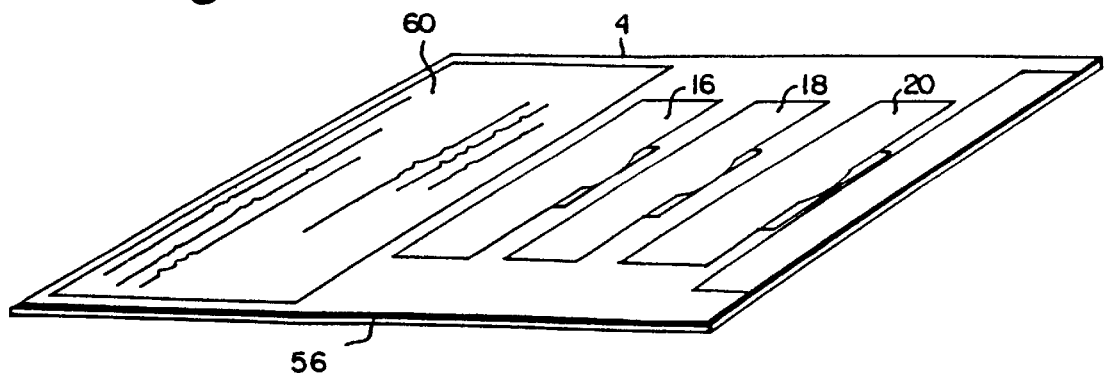
FIGS. 3a, 3b and 3c are an exploded view of the device of FIG. 1 showing the outer panels and the support panel carrying the sheet therebetween.
Figure 3B:
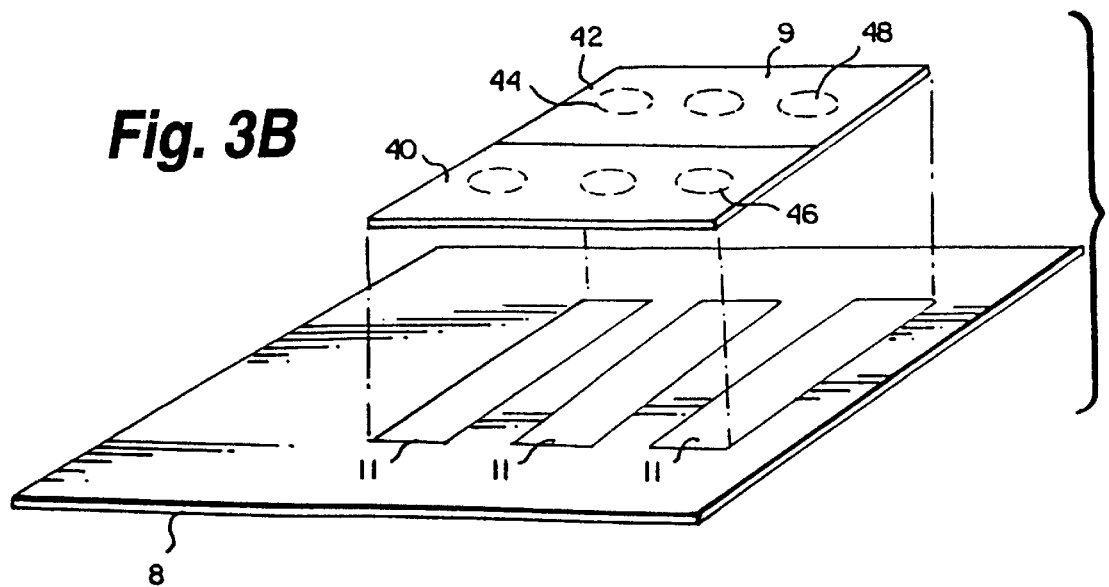
Figure 3C:
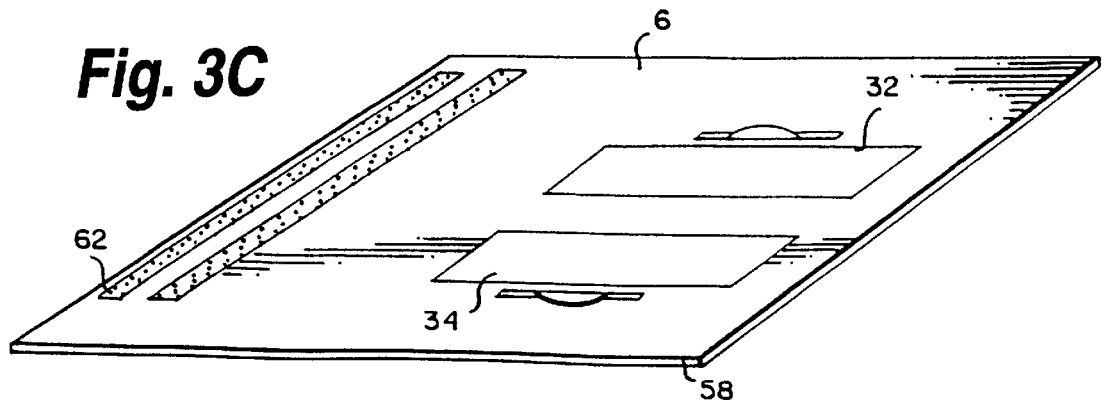

Referring to FIG. 3, FIGS. 3a and 3c show the first and second panels 4, 6 with the respective first and second covers overlying the apertures. In FIG. 3c, the second panel is oriented upwards for ease of viewing. FIG. 3b shows sheet 8 disposed between panels 4 and 6. In the embodiment illustrated, the sheet 9 is a single piece of filter paper having first and second portions 40, 42 separated from each other by a dividing region 44, which may comprise a hydrophobic material, for example wax. The first portion 40 is impregnated with the reagent and the second portion 42 is not impregnated with reagent. It is possible however for both portions to be impregnated with reagent provided impregnation of the second portion does not adversely affect any subsequent testing which might be conducted using the second portion. The first and second portions are visible through the apertures when the respective covers are in the open position. Each of the portions 40, 42 is provided with indicating means 46, 48, typically circular zones in dashed outline, in order to assist the user in knowing where to smear sample on the sheet. Moreover, the zones 48 have perforations 50 to enable the zones 48 to be removed from the sheet 9 for further analysis (described in more detail below).

The outer panels 4, 6 and the support panel 8 are preferably formed of paper or cardboard in which the apertures are die-cut along with perforations in the outer panels to form the covers. The panels could equally be made from other suitable materials such as a plastic material. A tab 52 is formed on each cover and is engageable with a slit 54 to maintain the cover in the closed position. The slit 54 may be formed during the die-cutting operation mentioned above.

The sheet 9 is typically cut from a length of filter paper with a repeating pattern of perforations 50 corresponding to the zones 48. The sheet 9 may be formed from one piece of filter paper with the hydrophobic dividing region 44 separating the first and second portions. Alternatively, the first and second portions may be two separate pieces of filter paper each constituting the first and second portions of the sheet, and separated by a hydrophobic region.

The device is assembled by overlying the panels 4 and 6 with the support panel 8 carrying the sheet 9 therebetween. The assembly is held together with a suitable glue or adhesive. In order to minimize sticking of the covers to the specimen, the panels 4 and 6 are provided on their inner surfaces 56, 58 with a layer of non-stick material, typically a wax layer. In this way, the perforated zones 48 carrying the specimen can be removed without them sticking to the inner surfaces of the covers on the first and second panels.

The panels 4, 6 and support panel 8 are assembled such that the apertures in the first panel and the support panel are opposite the apertures in the second panel, and the first and second portions on the sheet are aligned with the apertures in each panel. In this way, specimens placed on the sheet through the apertures in the first panel can be accessed and tested through the apertures in the second panel.

The first panel 4 may be provided with appropriate printed matter at the top and bottom to assist the user. For example, the patient's name, address and instructions on how to use the device may be printed at the top of the first panel in the region 60. Printed matter may also be provided at the top and bottom of the second panel. For example instructions to the doctor as to how to carry out testing by opening respective covers on the second panel 6 may be provided at 62.

In use, where a fecal sample is to be analyzed, a cover on the first panel 4 of the device is opened and a fecal specimen is smeared through the aperture on the first and second portions of the exposed sheet. The cover is then closed. A second fecal sample taken at a different time as a result of a different bowel movement is then smeared onto the first and second portions of the sheet through the second aperture on the first panel and the cover is closed.

The third specimen from yet a different bowel movement at a different time is smeared onto the first and second portions through the third aperture on the first panel and the cover is closed. To conduct a first analysis, the cover on the second panel covering the first portions on which specimen has been applied is opened and developer solution is applied to the circular zone 46 of each first portion. If a specimen tests positive, as evidenced, for example, by the development of a blue color, the cover on the second panel covering the second portions is opened together with the cover on the first panel, and the respective exposed perforated circular zone 48 of the second portion of the sheet carrying the positive specimen is removed with both covers open, e.g. by being punched out of the sheet, and subjected to further analysis (e.g. an immunochemical test).

Figure 4A:
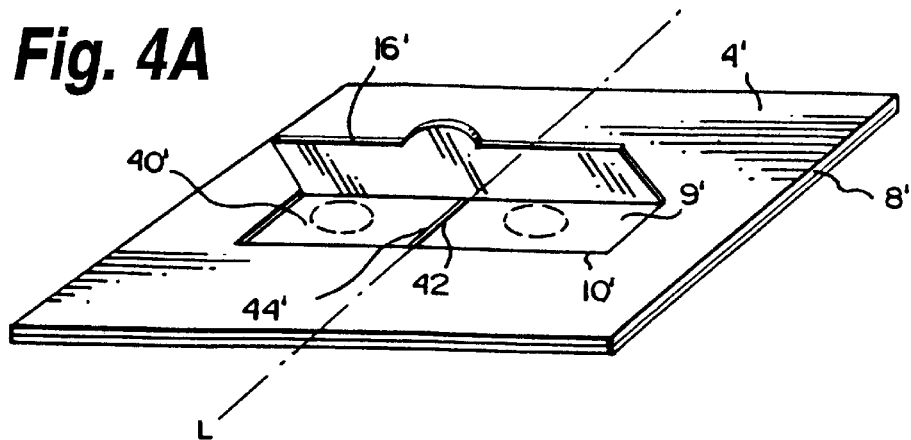
FIGS. 4a, 4b and 4c show perspective views of alternative embodiments of the device of the invention.
Figure 4B:
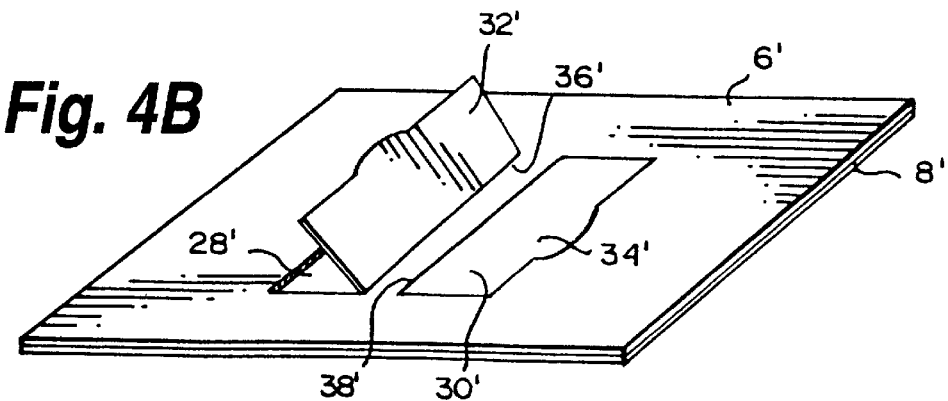

FIGS. 4a and 4b show an alternative embodiment of the device of the invention including a first panel 4' with one aperture 10' extending transversely of longitudinal axis L and a cover 16' overlying the aperture 10', a second panel 6' with two apertures 28', 30' each with an independently moveable cover 32', 34' hingedly mounted along hinge lines 36', 38' extending parallel to axis L, and a support panel 8' positioned between the first and second panels with a sheet 9' having first and second portions 40', 42' divided by a dividing region 44'. The covers on the first and second panels overlie the first and second portions 40', 42' of sheet 9'.

Figure 4C:
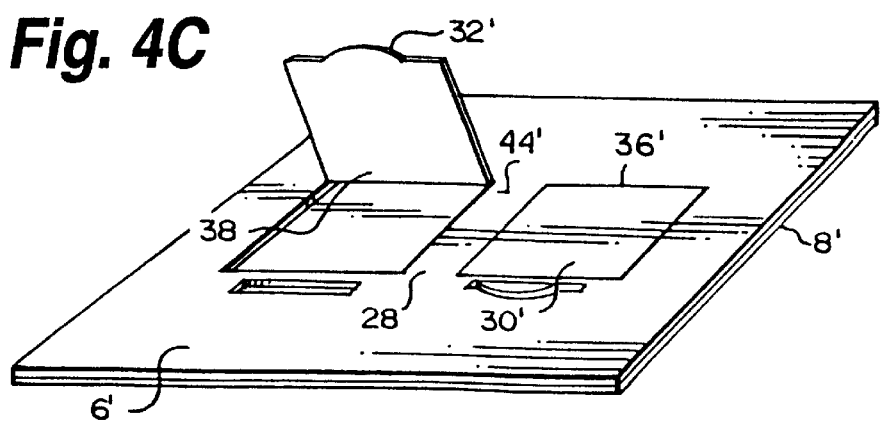

FIG. 4c shows a structural variation of the device of FIGS. 4a and 4b where the second panel 6' has a single transversely extending aperture 28' opposite the single aperture in the first panel with two independently moveable covers 30', 32' hingedly mounted along hinge lines 36', 38' extending transversely of axis L. The device of FIG. 4a–4c is constructed and used in the same manner as for the embodiment described with reference to FIGS. 1–3, and is adapted for situations where it is not necessary to collect and analyze a plurality of specimens.

Further modifications of the invention will be readily apparent to those skilled in the art. For example, the invention has been described above with reference to the preferred embodiment where three transversely extending rectangular apertures are present in the first panel 4 and two longitudinally extending rectangular apertures are in the second panel 6. The invention, however, is not limited to devices comprising three apertures in the first panel. Embodiments comprising fewer apertures in the first and second panels are described above. Other embodiments with more or less than three apertures in the first panel may be constructed and used as the analytical situation demands.

In the above description, the apertures are illustrated as rectangular. However, any desired shape may be used, for example oval or circular.

The device has been described as including a support panel 8. However, it is possible, depending on the dimensions of the device and the thickness of the filter paper, to dispense with the support panel and place the sheet 9 directly between the first and second panels 4, 6.

FIGS. 5 through 8 show alternative embodiments of the invention. In a first aspect, illustrated in FIGS. 5 and 6, there is shown a foldable panel 70 of the invention. The panel is typically made of paper or cardboard, but may also be fabricated of plastic. The panel has a first outer side 72 and an opposite inner side 74. The panel 70 has a fold line 76 extending along a longitudinal axis 78 forming a first portion 80 on one side of the fold line and a second portion 82 of the other side of the fold line. The first portion 80 is provided with three rectangular apertures 84, 86, 88 extending transversely with respect to the longitudinal axis 78. Each aperture has a respective cover 90, 92, 94 hingedly mounted to the first portion 80 along a respective hinge line 96, 98, 100 extending longitudinally of the axis 78. Each cover 92, 92, 94 is hingedly movable independently of the others between closed and open positions, similar to that shown in FIG. 1.

The second portion 82 includes two rectangular apertures 102, 104 extending longitudinally of the axis 78 and opposite the transversely extending apertures 84, 86, 88. Aperture 102 is provided with a cover 106 and aperture 104 provided with a cover 108. Covers 106 and 108 are each hingedly mounted along a respective hinge line 110, 112, each of which extends longitudinally of the axis 78. Each cover 106, 108 is movable independently of the other between a closed portion and an open portion, similar to that shown in FIG. 2.

The first portion 80 is provided with locations 114 for completion of date(s) on which samples are collected from the patient and patient identifying information 116. In addition, each cover 92, 92, 94 is provided with specimen identification information 118 together optionally with instructions for application of a specimen sample after the cover is opened.

The second portion 82 is provided with locations 120 for reporting results of testing, together with boxes 122 for completion of action taken with respect to the patient and/or doctor. The covers 106, 108 are provided with respective information 124, 126 regarding person or entity conducting analysis of the specimen. Tabs 107 are formed on each cover to assist the user in opening the cover.

Figure 6:
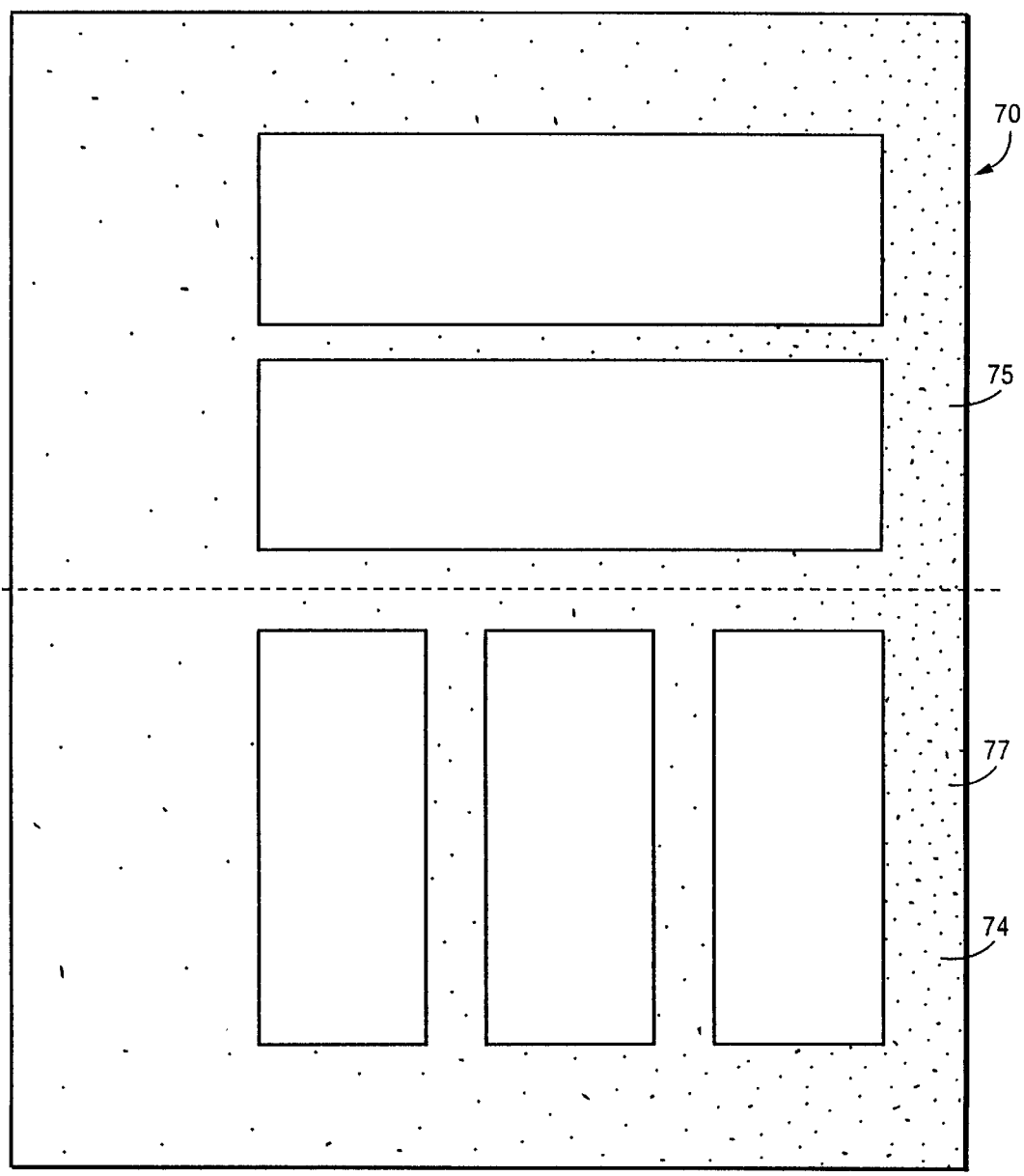
FIG. 6 is a plan view of the inside configuration of the foldable panel of FIG. 5.

FIG. 6 shows the other (inner) side 74 of the panel 70. The surfaces 75, 77 are typically coated with a hydrophobic material, preferably a waterproof glue such as wax containing an adhesive. The purpose of this hydrophobic material is to prevent contamination or mixing of individual specimens applied through an aperture into the region of an adjacent aperture. In this way, the risk of a specimen spreading and contacting other specimen(s) is minimized. The hydrophobic material also aids in minimizing sticking of the covers to the specimen.

Figure 7:
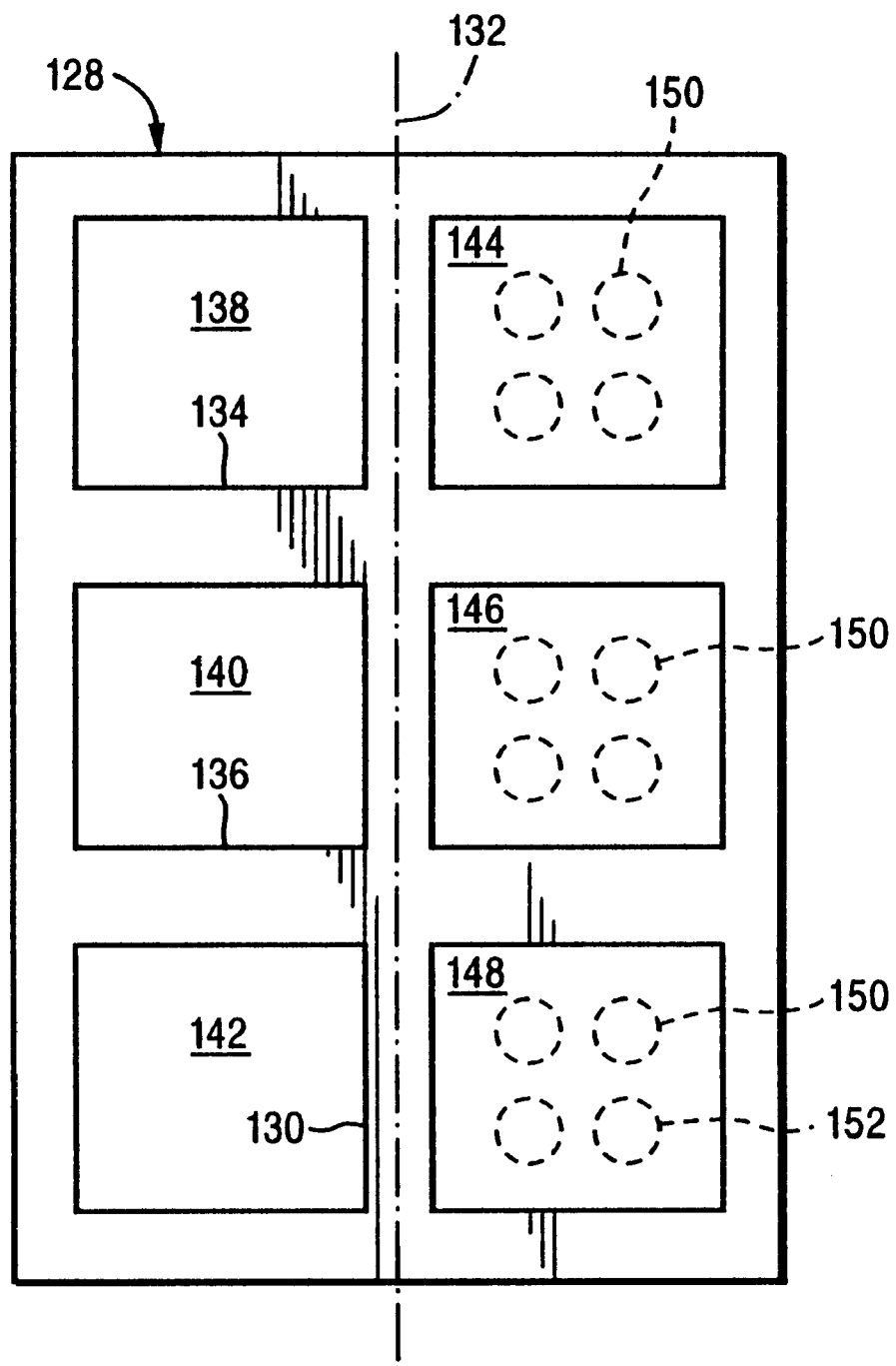
FIG. 7 is a plan view of a simple receiving sheet which is positionable inside the foldable panel of FIG. 5 when the latter is folded.

FIG. 7 shows a sample receiving sheet 128 sized to be received between portions 80, 82 when folded over each other. Sheet 128 is typically made of an absorbent material, usually filter paper, which is impregnated with a reagent which will react with hemoglobin components from blood and a peroxide solution to form a colored compound. Examples of suitable reagents are given above in connection with the discussion of sheet 9 shown in FIG. 3(*b*). To prevent seepage of reagent from one area to another, sheet 128 is provided with a strip of hydrophobic material 130 such as wax extending longitudinally along axis 132 and two strips of hydrophobic material 134, 136 such as wax extending transversely of axis 132 and crossing strip 130. The intersecting pattern of strips 130, 134, 136 defines six regions 138, 140, 142, 144, 146, 148. Regions 144, 146, 148 are each provided with indicating means 150, typically circular zones shown in dashed outline to assist the user in browsing where to smear the sample on the sheet. The zones may be provided with perforations 152 to enable the zones to be removed from the sheet 128 for subsequent analysis. As with sheet 9 discussed above the sheet 128 may, if desired, be supported on a support member (not shown).

The sheet 128 may be formed from one piece of absorbent paper with hydrophobic strips defining the regions 138–148. Alternatively, the sheet 128 may be constructed from different absorbent papers, each optionally containing different reagents, with the hydrophobic strips bonding the different papers together to form the sheet. In a further modification, the six regions 138, 140, 142, 144, 146, 148 may be comprised of different paper(s) of varying textures, and carrying different colors of reagent. Each region is then bonded together with hydrophobic material to form the completed sheet 128.

The term "texture" as used herein in connection with the sheet 128 means that the fibrous structure of the sheet material, e.g. paper, may be varied depending on the desired degree of adherence of the sample. The paper should be sufficiently absorbent so that specimen does not easily separate from the sheet after application thereto, for example as the specimen dries out. Generally, the sheet (paper) is chosen such that the fibrous structure of the paper permits at least some of the sample to permeate through the paper and be visible on the other side to that on which the specimen is applied. Generally, the sheet material should be such that at least about 20% by weight, for example about 25 to about 50% by weight, of the specimen permeates through the sheet and is visible on the other side.

Figure 8:
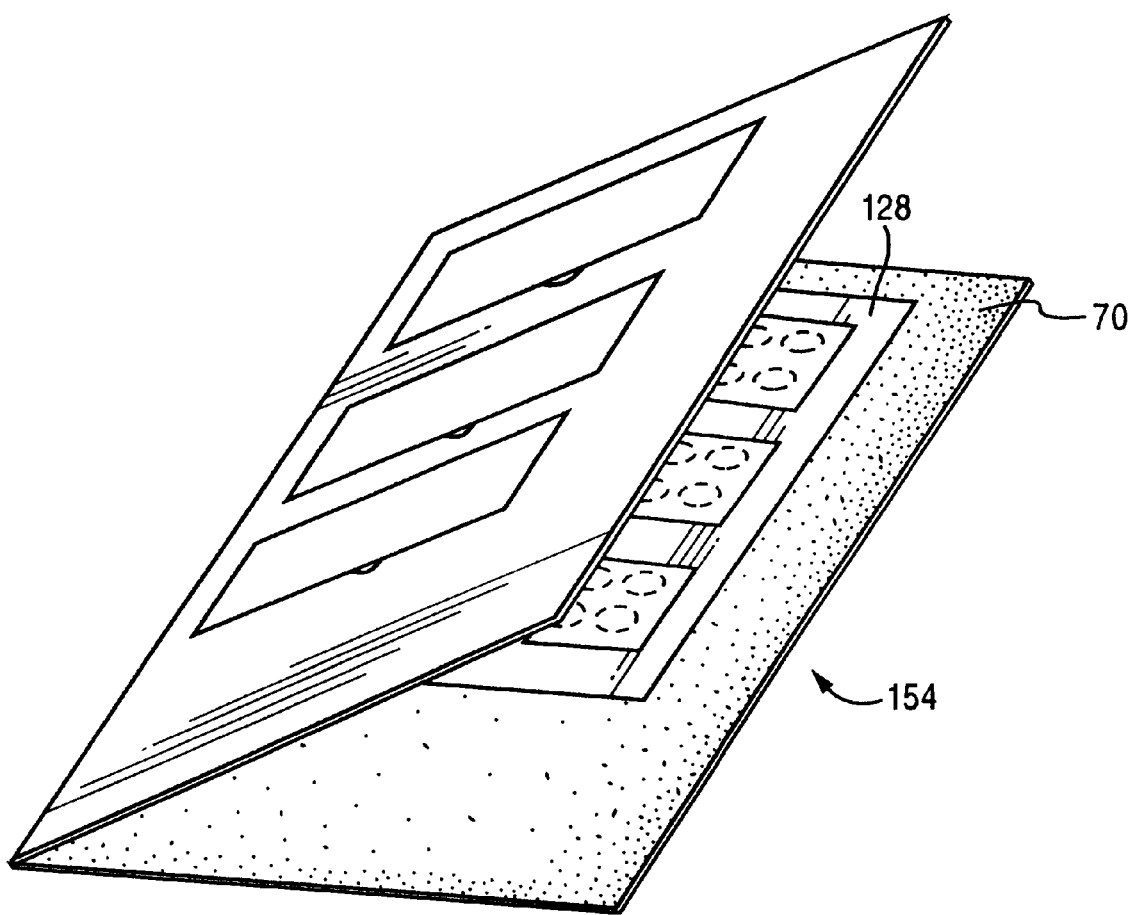
FIG. 8 is a perspective view of the embodiment in partially open configuration comprised of a foldable panel of FIGS. 5 and 6 and a sample receiving sheet of FIG. 7 therebetween.

FIG. 8 is a device 154 of the invention constructed using a foldable panel 70 and a sheet 128. The device is constructed placing a sheet 128 on an inside surface 74 with the regions 138–148 aligned with apertures 84, 86, 88. The panel 70 is then folded along fold line 76 to bring the inner surface 74 into face-to-face contact with each other, sandwiching the sheet 128 therebetween with regions in registration with apertures 84, 86, 88 and apertures 102, 104. The adhesive present on surfaces 74 permits the surface to be adhered to each other to maintain the resulting device in the folded closed state.

The device 154 is used in the same way as described above for the device illustrated in FIGS. 1–3.

The invention has been described with reference to analysis of fecal samples for stool occult blood. However, the device may be used for screening and testing of other biological specimens, for example blood and AIDS tests, urine tests and pregnancy tests.

While the present invention has been described in considerable detail, the invention disclosed herein is not limited to the detailed description, and is to be afforded the full scope of the appended claims and all equivalents thereto.

What is claimed is:

1. A specimen testing device, comprising:

first panel;

an aperture in said first panel;

a second panel mounted opposite to said first panel;

a second and third aperture in said second panel opposite said first aperture in said first panel, said first and second panels having a first longitudinal axis;

a sheet disposed between said first and second panels for receiving a specimen through said first aperture, said sheet in said first aperture having first and second portions disposed on opposite sides of a second longitudinal axis of said sheet for receiving the specimen, said first portion containing a reagent for reaction with the specimen, said first aperture extending across said first and second portions;

a first aperture cover mounted on said first panel and overlying said first aperture in said first panel, said first aperture cover being hingedly mounted along a hinge line extending transversely of said first longitudinal axis;

a second aperture cover mounted on said second panel and overlying said first portion of said sheet;

a third aperture cover mounted on said second panel and overlying said second portion of said sheet, said second and third aperture covers on said second panel being hingedly mounted along a hinge line extending parallel to said first longitudinal axis;

wherein opening of said second aperture cover on said second panel exposes said first portion containing said reagent for reaction with said specimen, and opening of said third aperture cover on said second panel exposes said second portion for further analysis of the specimen received thereon.

2. The device according to 1, wherein said apertures in said first and second panels are rectangular.

3. The device according to claim 1, wherein said first aperature cover is hingedly mounted along a hinge line extending transversely of said first longitudinal axis.

4. The device according to claim 1, wherein said first and second portions are divided by a dividing region.

5. A device according to claim 1, wherein said second portion is provided with indicating means for locating where the specimen is to be placed on the sheet.

6. The device according to claim 1, wherein said first panel has three apertures extending transversely of said first longitudinal axis and said second panel has two apertures extending parallel to said first longitudinal axis, said apertures in said second panel being opposite said apertures in said first panel.

7. The device according to claim 1, wherein said first and second panels have printed matter thereon.

8. The device according to claim 1, wherein an inner surface of said first aperture cover on said first panel and said second and third aperture covers on said second panel are provided with a non-stick wax layer.

9. The device according to claim 1 wherein said sheet is supported on a support panel disposed between said first and second panels.

10. The device according to claim 4, wherein said dividing region comprises a hydrophobic strip.

11. The device according to claim 5, wherein at said indicating means is comprised of a zone which is removable from said sheet.

12. The device according to claim 6, where each of said three apertures in said first panel has a respective cover and wherein a fourth aperture cover is hingedly mounted on said second panel along a hinge line extending parallel to said first longitudinal axis and overlies said first portion of said sheet and wherein a fifth aperture cover is hingedly mounted on said second panel along a hinge line extending parallel to said first longitudinal axis and overlies said second portion of said sheet, said fourth and fifth aperture covers being selectively movable with respect to each other to expose said first and second portions of said sheet.

13. The device according to claim 11, wherein said zone is defined by perforations.

14. The device according to claim 11, wherein said third aperature cover overlies said removable zone.

15. A method of analyzing a specimen using a specimen testing device including a first panel; an aperture in said first panel; a second panel mounted opposite to said first panel; a second and third aperture in said second panel opposite said first aperture in said first panel, said first and second panels having a first longitudinal axis; a sheet disposed between said first and second panels for receiving a specimen through said first aperture, said sheet in said first aperture having first and second portions disposed on opposite sides of a second longitudinal axis of said sheet for receiving the specimen, said first portion containing a reagent for reaction with the specimen, said first aperture extending across said first and second portions; a first aperture cover mounted on said first panel and overlying said first aperture in said first panel, said first aperture cover being hingedly mounted along a hinge line extending transversely of said first longitudinal axis; a second aperture cover mounted on said second panel and overlying said first portion of said sheet; a third aperture cover mounted on said second panel and overlying said second portion of said sheet, said second and third aperture covers on said second panel being hingedly mounted along a hinge line extending parallel to said first longitudinal axis; wherein opening of said second aperture cover on said second panel exposes said first portion containing said reagent for reaction with said specimen, and opening of said third aperture cover on said second panel exposes said second portion for further analysis of the specimen received thereon;

said method comprising:
 (a) obtaining the specimen;
 (b) opening the first aperture cover on said first panel to expose said first and second portions of said sheet;
 (c) smearing a portion of said specimen on said first and second portions of said sheet through said first aperture;
 (d) closing said first aperture cover to overlie said first aperture of said first panel;
 (e) opening said second aperture cover on said second panel to expose said first portion of said sheet carrying said specimen and said first reagent;
 (f) applying a second reagent to said exposed first portion of said sheet;
 (g) observing a color change corresponding to a positive test condition upon reaction of the first reagent with the specimen;
 (h) selectively opening said third aperture cover on said second panel and removing said second portion of said sheet, wherein the specimen is subjected to further testing.

16. The method according to claim 15, wherein a zone of said second portion is removed from said sheet for further analysis.

17. The method according to claim 15, wherein the specimen is a fecal specimen.

* * * * *